(12) United States Patent
Hallouin

(10) Patent No.: US 9,241,844 B2
(45) Date of Patent: Jan. 26, 2016

(54) STRUCTURE WITH A REUSABLE ABSORBENT LAYER AND ASSOCIATED SLEEVE

(75) Inventor: Florence Hallouin, Paris (FR)

(73) Assignee: GENERATION PLUME, Paris (FR)

( * ) Notice: Subject to any disclaimer, the term of this patent is extended or adjusted under 35 U.S.C. 154(b) by 925 days.

(21) Appl. No.: 13/145,210

(22) PCT Filed: Jan. 20, 2010

(86) PCT No.: PCT/FR2010/050087
§ 371 (c)(1),
(2), (4) Date: Sep. 13, 2011

(87) PCT Pub. No.: WO2010/084285
PCT Pub. Date: Jul. 29, 2010

(65) Prior Publication Data
US 2012/0029459 A1      Feb. 2, 2012

(30) Foreign Application Priority Data

Jan. 20, 2009   (FR) ...................................... 09 00240

(51) Int. Cl.
*A61F 13/15*     (2006.01)
*A61F 13/494*    (2006.01)
(Continued)

(52) U.S. Cl.
CPC ..... *A61F 13/49413* (2013.01); *A61F 13/49004* (2013.01); *A61F 13/4906* (2013.01); *A61F 13/505* (2013.01); *A61F 13/72* (2013.01); *A61F 2013/49433* (2013.01)

(58) Field of Classification Search
CPC ......... A61F 13/74; A61F 13/76; A61F 13/78; A61F 13/80; A61F 13/505; A61F 13/49003; A61F 13/49473; A61F 13/49058; A61F 13/4906; A61F 13/49061; A61F 2013/49063; A61F 2013/49068; A61F 2013/49069; A61F 13/68; A61F 13/72
USPC ........................................... 604/393, 397–400
See application file for complete search history.

(56) References Cited

U.S. PATENT DOCUMENTS 3,400,718 A * 9/1968 Saijo .............................. 604/394
3,771,524 A * 11/1973 Ralph ........................... 604/398
(Continued)

FOREIGN PATENT DOCUMENTS

EP       0 374 542 B1    11/1994
FR       2578163         9/1986
(Continued)

OTHER PUBLICATIONS

International Search Report as issued for PCT/FR2010/050087.

*Primary Examiner* — Lynne Anderson
*Assistant Examiner* — Bradley Philips
(74) *Attorney, Agent, or Firm* — Pillsbury Winthrop Shaw Pittman LLP

(57) ABSTRACT

A reusable absorbent diaper type structure having a longitudinal axis XX and including an outer support element which can be adjusted to the body of a user, a flat absorbent element and an intermediate impervious element for supporting the absorbent element, the intermediate element being connected by connectors to the outer element. The intermediate element exhibits on each of the lengths thereof an elastic border, which, in the stretched and flattened state, makes it possible to cover the absorbent element according to at least a longitudinal area, and when the structure is positioned on the user, is liable to remain in permanent contact with the skin of the user.

18 Claims, 6 Drawing Sheets

(51) Int. Cl.
*A61F 13/72* (2006.01)
*A61F 13/505* (2006.01)
*A61F 13/49* (2006.01)

(56) References Cited

U.S. PATENT DOCUMENTS

| | | | | |
|---|---|---|---|---|
| 4,597,760 | A * | 7/1986 | Buell | 604/397 |
| 4,846,825 | A * | 7/1989 | Enloe et al. | 604/385.22 |
| 5,187,817 | A * | 2/1993 | Zolner | 2/400 |
| 5,217,447 | A * | 6/1993 | Gagnon | 604/397 |
| 5,360,422 | A * | 11/1994 | Brownlee et al. | 604/385.15 |
| 5,725,518 | A * | 3/1998 | Coates | 604/391 |
| 5,891,122 | A | 4/1999 | Coates | |
| 6,010,490 | A * | 1/2000 | Freeland et al. | 604/385.19 |
| 6,682,515 | B1 * | 1/2004 | Mizutani et al. | 604/385.27 |
| 6,706,029 | B1 | 3/2004 | Suzuki et al. | |
| 6,926,705 | B1 | 8/2005 | Coates | |
| 2006/0116656 | A1 * | 6/2006 | Hendren et al. | 604/396 |
| 2007/0255248 | A1 * | 11/2007 | Hendren et al. | 604/395 |
| 2008/0195070 | A1 * | 8/2008 | Ponomarenko et al. | 604/378 |
| 2008/0215028 | A1 * | 9/2008 | Brown et al. | 604/385.15 |
| 2009/0312730 | A1 * | 12/2009 | LaVon et al. | 604/365 |
| 2009/0312737 | A1 * | 12/2009 | LaVon et al. | 604/385.26 |
| 2010/0274211 | A1 * | 10/2010 | Beck et al. | 604/385.19 |

FOREIGN PATENT DOCUMENTS

| | | |
|---|---|---|
| FR | 2872028 | 12/2005 |
| WO | WO 95/10992 | 4/1995 |
| WO | WO 2005/084601 | 9/2005 |
| WO | WO 2008/126438 | 10/2008 |

* cited by examiner

STRUCTURE WITH A REUSABLE ABSORBENT LAYER AND ASSOCIATED SLEEVE

CROSS REFERENCE TO RELATED APPLICATIONS

This application is the U.S. National Stage of PCT/FR2010/050087, filed Jan. 20, 2010, which in turn claims priority to French Patent Application No. 0900240, filed Jan. 20, 2009, the entire contents of all applications are incorporated herein by reference in their entireties.

TECHNICAL FIELD OF THE INVENTION

The invention relates to the field of external body hygiene and more particularly to the structures or articles intended for absorbing and retaining bodily secretions.

The products aimed by the invention particularly relate to diapers for babies, children, diapers for incontinent adults and other equivalent products.

In this field there are several families of products: historically, the washable products have existed for a long time particularly diapers or swathes constituted of large squares of gauze or flannelette to be folded depending on the morphology of the wearer. The swathes are fastened using a pin or another reversible attachment system then are generally surrounded with an impervious plastic material. This solution is undoubtedly economical as it is reusable ad infinitum, but it is very restrictive as it requires frequent washing. Moreover, the fact of having to fold a square of cotton fabric and to fasten it with a pin or any other attachment means makes this system complicated to put on the user and requires a certain dexterity particularly on the body of a moving baby. Furthermore, this type of product induces leaks.

It is also known for example, from document FR 2 872 028 pre-formed diapers that have an anatomical shape, and which are elasticated, particularly at the thighs and in the back of the wearer. These diapers are generally provided with a reversible closing system such as self-gripping strips or press studs. It is provided to insert between the inner side and the outer side of these diapers a removeable absorbent element. This solution may reduce the drying time with respect to the washable products made from one single piece. Moreover, although it is easier to use than swathes, this solution has drawbacks particularly pertaining to their hold and tightness.

It is further known U.S. Pat. No. 6,926,705 which describes a washable underwear formed by an inner pocket connected to an intermediate envelope being itself connected to an outer impervious envelope. The inner pocket exhibits a border fitted with an elastic extending on the entire or a part of its inner edge with a covering of the absorbent element.

A tightness issue may result from the presence of a soft intermediate and usually absorbent material between the pocket and the outer envelope which, in contact with the edges of the pocket may leak by capillary action, as well as at the stitches particularly between the pocket and the underwear. Another tightness issue may result from the movements from the sitting and standing positions of the wearer as well as the weight due to the liquid contained in the structure, the assembly may sag and leaks may occur at the crotch. This solution of the prior art does not achieve a permanent contact between the intermediate element and the skin of the user.

One also knows in the state of the art the patent EP374542 as well as the international patent application WO95/10992.

The latter document discloses an absorbent diaper comprising an outer washable element which can be adjusted to the body of the user.

U.S. Pat. No. 5,891,122 describes a complex diaper whereof the intermediate element does not ensure good tightness.

The washing issue of the diapers and equivalent products has been radically resolved by the arrival of disposable single use products. Innumerable documents, particularly patent applications, testify to a sustained activity in this field for several years now.

The diapers or disposable articles usually comprise a mass which absorbs the liquids arranged between a permeable veil on the side of the body and an impervious paper for example in polyethylene on the outside. The French patent FR 2 578 163 discloses an example of this type of solution.

The fact that these products are single use ones leads of course to an important consumption and consequently a cost which can become burdensome in a family budget.

Low cost disposable diapers have been developed and commercialized however, they sometimes lead to irritation issues for babies skins and/or leaks.

Moreover, the disposable products must be eliminated in one way or another. If they are thrown in the garbage, they naturally increase its volume and their treatment thus represents a cost and an energy expenditure which may prove to be considerable. Thus environment-wise, constraints are induced by these single use products. Furthermore, if the articles which are generally cellulose wadding-based are thrown into the sewer, they must necessarily be disintegratable so as not to block said sewer. This characteristic itself has a cost.

Intermediary issues between these two great families are known.

By way of illustration, the patent application WO 2008/030984 shows a reusable diaper comprising a permeable inside diaper and a impervious outside diaper between which it is possible to removeably interpose an absorbent insert. A ventral slit is provided for this. The insert may itself be washable, or disposable; the inside and outside layers constituting this diaper are reusable but must necessarily be washed upon every use, hence, a particularly important maintenance.

A similar concept is illustrated in the patent application WO 2005/084601 which discloses a plane impervious pocket of substantially oval shape, able to enclose an absorbent element. This pocket is possibly provided with means enabling it to be removeably fastened inside underwear. Here, it consists in only changing the absorbent element which may be disposable or reusable.

Such a solution seems unreliable as to its tightness particularly as the pocket is not sufficiently maintained against the body of the user.

By "user" it is to be understood the wearer of the absorbent structure.

SUMMARY OF THE INVENTION

The invention aims to remedy to the drawbacks of the state of the art and particularly to propose articles or structures of reusable absorbent diaper that are at the same time comfortable, impervious and easy to use. Being entirely or partially reusable, this type of product is primarily economical and environment friendly.

For this, the invention, according to its more general acceptance, relates to a reusable absorbent diaper type structure, having a longitudinal axis XX and comprising an outer support element which can be adjusted to the body of a user, a flat absorbent element and an intermediate impervious element for supporting the absorbent element, the intermediate element being connected by an attachment means to the outer element characterized in that the intermediate element exhibits on each of the lengths thereof an elastic border which, when in the stretched and flattened state, makes it possible to cover at least a longitudinal area of the absorbent element characterized in that the dimension of the outer element measured along axis XX and between said attachment means, is lower than the dimension of the element of the intermediate element measured along the same direction XX, between said attachment means, such that the intermediate border remains in permanent contact with the skin of the user.

It is meant by "dimension of the outer element measured along the axis XX and between said attachment means" in the present patent the length measured on a longitudinal median line of the fabric constituting the outer element, when this outer element is flattened without the tightening areas at the apertures for the passage of the thighs. The ends of this line are the intersection between the longitudinal axis XX and the transversal axis (thus perpendicular) passing by the attachment means respectively ventral and dorsal ensuring the connection between the outer element and the intermediate element.

It is meant by "dimension of the element of the intermediate element measured along the same direction XX" in the present patent, the length measured on the median longitudinal line of the fabric constituting the intermediate element, when this intermediate element is flattened, without elastics. The ends of this line are, as for the dimension of the outer element; defined by the intersections between the longitudinal axis XX and the transversal axis (thus perpendicular) passing by the attachment means respectively ventral and dorsal ensuring the connection between the outer element and the intermediate element.

It is meant by "less" in the present patent, the differences in lengths such as defined in the two previous paragraphs sufficient for the outer element to ensure the maintenance of the intermediate element in a way such as to guarantee the permanent and continuous contact, between the lateral edges of the intermediate element and the skin of the user. This function leads to the result of a good tightness of the intermediate element and an absence of leaks.

The invention particularly relates to a reusable absorbent diaper type structure, having a longitudinal axis XX and comprising an outer support element which can be adjusted to the body of a user, a flat absorbent element and intermediate impervious element for supporting the absorbent element, the intermediate element being connected by attachment means to the outer element. According to the invention, the intermediate element exhibits on each of its lengths an elastic border which, in the stretched and flattened state, makes it possible to cover the absorbent element according to at least one longitudinal area and when the structure is positioned on the user, is liable to remain in permanent contact with the skin of the user.

This execution allows for, by its modularity, different types of usage depending on the needs and/or aspirations of the user.

Furthermore, said border exhibits in the stretched and flattened state, a convexity facing towards the longitudinal axis XX.

This characteristic reinforces the tightness and the hold of the structure on the body of the user.

Furthermore, the dimension of the outer element measured along the axis XX and between said attachment means is lower than that of the intermediate element; and the dimension of the outer element measured perpendicularly to the axis XX may be lower than that of the intermediate element at the crotch.

Preferably, the maximum distance H measured perpendicularly to the longitudinal axis XX, between the elastic border and the longitudinal edge of the absorbent element is greater than 3 cm.

These dimensional characteristics make it possible, on the one hand for the outer element to become tightly adjusted to the intermediary element and on the other hand to not interpose, at the crotch, between the skin of the user and the intermediary element.

Furthermore, whatever the position of the user, there remains a contact with the elastic edge of the diaper whatever the state (dry or humid) thereof.

According to another aspect, the outer element is reusable, preferably washable and may be furthermore, elastic.

Furthermore, the absorbent element may be reusable. While remaining within the framework of the invention, the absorbent element may be disposable.

Preferably, the attachment means of the intermediate element on the outer element are arranged according to the width of the absorbent element and comprise reversible attachment elements. This characteristic has the advantage of having a great suppleness of use as one may thus temporarily detach these two elements in order to for example wash them separately, and/or replace one of them by another which is clean for the use.

Within the frame of the invention, the attachment means are arranged according to the width of the absorbent element and comprise non removeable attachment elements.

More specifically, the outer element has a general X shape and comprises a symmetrical axis X'X' which coincides with the longitudinal axis XX of the structure.

Furthermore, the outer element has at least a non expansible mechanical reinforcement area in dorsal contact with the user, symmetrical with respect to the axis XX and preferably butterfly-shaped.

An interesting feature of the invention consists in that the structure further comprises a disposable sleeve covering at least the surface of the absorbent element in contact with the skin of the user.

Furthermore, the intermediate element may comprise longitudinal wings connected to each of its elastic longitudinal edges. This, characteristic reinforces the tightness between the structure and the body particularly at the crotch.

According to another of its aspects, the invention covers a disposable sleeve intended to envelop an absorbent element that is part of a reusable absorbent diaper type structure. As it will be explained in further detail hereinafter, the sleeve represents a barrier for certain bodily secretions, particularly fecal matter but it lets pass urine and other fluids which are thus directed towards the actual absorbent element.

BRIEF DESCRIPTION OF THE FIGURES

Other characteristics, details and advantages of the invention will become apparent upon reading the following description with reference to the accompanying drawings, which illustrate.

For more clarity, the identical or similar elements are marked by identical reference signs in all the figs.

DETAILED DESCRIPTION OF AN EMBODIMENT

Figure 1:
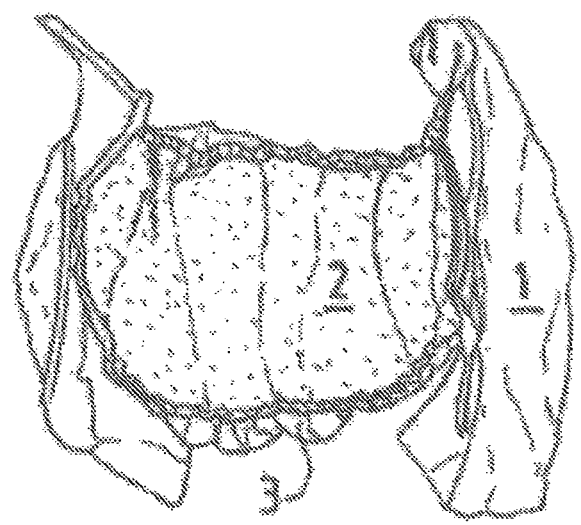
FIG. 1, a top view of the structure according to the invention in usage position.

FIG. 1 illustrates a first embodiment of a structure according to the invention which particularly comprises an outer support element 1 which can be adjusted to the body of a user. The element 1 is qualified here of outer as opposed to the other elements that constitute the invention and particularly with respect to a flat absorbent element 2 that is in direct contact with the body of the user. In this respect, the absorbent element 2 is "inner" as it is in direct contact with the body of a user. Between these two elements, is provided an intermediate impervious element 3 intended on the one hand to support the absorbent element and on the other hand to ensure the connection between the absorbent element and the outer element 1.

The outer element may be adapted to the body of the wearer by fasteners, press studs, gripping elements or other, arranged at the waist of the wearer.

Within the framework of the invention, the outer element 1 may be knickers i.e., a piece that is directly adapted on the waist of the wearer and comprises an aperture for each thigh.

The structure in its entirety exhibits a longitudinal axis XX.

Figure 2:
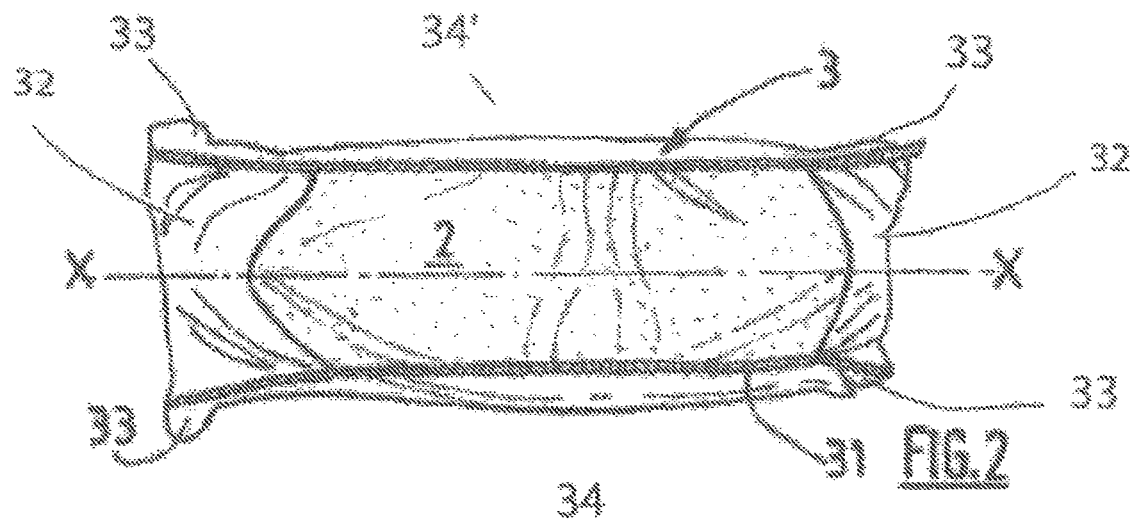
FIG. 2 a top view of the intermediate element and the absorbent element according to the invention, in extended position.

FIG. 2 shows the absorbent element 2 and the intermediate element 3 in stretched position, for a better understanding of the invention. It may be seen on this fig. that the assembly is stretched according to its length; the length is defined relatively to the absorbent element 2 which can exhibit a rectangular or a substantially rectangular shape, with a length (or large dimension) according to axis XX. The matter constituting the absorbent element 2 may be of disposable and degradable type, for example cellulose-wadding based. This aspect will not be described further as it is mastered by the skilled person, according to the selected parameters: absorption, tensile strength, suppleness, softness, disintegratable. Within the framework of the invention, the absorbent element may be reusable, particularly washable.

The intermediate element 3, which makes it possible to support the absorbent element 2, constitutes a type of shell open on the largest surface of the absorbent element 2. The intermediate element 3 exhibits two longitudinal elastic borders 31. Any means known per se such as a hemline fitted with an elastic ribbon may constitute said elastic border. Furthermore, the intermediate element 3 comprises two flaps 32 on the two ends of its width, which constitute means for supporting the absorbent element 2. Any other supporting means may be provided within the framework of the invention.

The intermediate element 3 is preferably constituted of an impervious and supple matter which the skilled person will easily choose according to his general knowledge.

Advantageously, the longitudinal borders 31 of the intermediate element 3 exhibit in the stretched state (as on FIG. 2) a convexity facing towards the longitudinal axis XX, such that the two longitudinal areas 34, 34' cover the absorbent element 2. As it will be further explained hereinafter, this feature improves the tightness of the structure according to the invention.

Furthermore, attachment means 33 are provided between the intermediate element 3 and the outer element 1. These means may be reversible i.e., allow for a temporary connection; studs or even gripping strips may be provided to this end. Multiple other solutions may be proposed within the framework of the invention.

Thus, the attachment means 33 may be constituted of a semi rigid strip fixed for example by stitching or by thermowelding on each width of the intermediate element and which surpasses by a few centimeters at each end. The attachment means 33 are arranged at each longitudinal end of the intermediate element 3 and in the vicinity of each end of the outer element 1. On the outer element 1 is fixed in at least two points a non expansible ribbon or fine cord type supple element. The distance between the two points is constant. The two points are spaced apart at a distance that is equal or even very slightly higher than the length of the stitching of the non expansible strip on the intermediate element 3. Thus, said semi rigid strip is interposed between said ribbon and inner side of the outer element 1. The semi rigid strip is compressed between the two points, thus creating a curvature. The curvature or more specifically the "cord" connecting the two ends contributes in deforming the diaper at this point and holding it in contact with the body of the wearer. Furthermore, this deformation maintains the intermediate element 3 against the outer element 1 when this assembly is not in place on the body of the wearer. The two elements 1 and 3 are thus deformed in the same manner and their respective curvatures particularly in the back and at the front of the structure are confounded.

According to this arrangement, at the waist of the wearer, is found successively at the outside towards the skin of the user: the outer element 1, the semi rigid strip, the supple ribbon and the intermediate element 3. The semi rigid strip thus being interposed, it is pressed against the user, thus to perfectly support the intermediate element 3. Moreover, these attachment means are very easy to put in place; they can advantageously be removed with one hand, the other hand remaining free for example to hold the baby.

According to another embodiment, the attachment means between the intermediate element 3 and the outer element 1 may be final fixings such as stitching, welding, glue lines . . . .

In all cases, the attachment means 33 are arranged according to the width and in the vicinity of the two ends of the absorbent element 2 when it is in place in the intermediate element 3.

The absorbent element 2 may further be constituted of a reusable matter, particularly washable. Thus, it is possible to reuse this element ad infinitum.

Furthermore, according to an embodiment, the absorbent element 2 being of rectangular shape, it is very easy to obtain from a mere folding of the fabric. Obviously, the fabric may be chosen by the user and/or provided by the manufacturer.

The user has thus the capability to choose himself/herself what constitutes the absorbent element 2, and that the latter be disposable or reusable.

Figure 3:
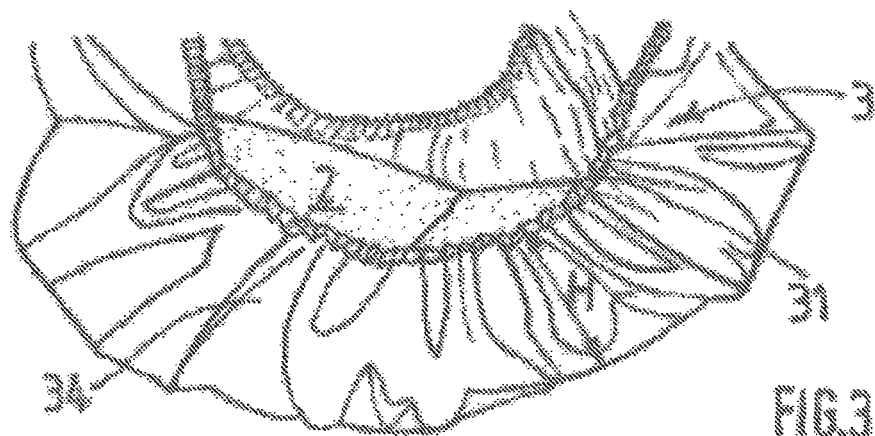
FIG. 3 a side view of the intermediate element in usage position.

FIG. 3 shows more precisely the intermediate element with the absorbent element in place inside, in usage position. One may see that each of said longitudinal areas 34 exhibits a certain height H measured between the elastic border 31 and the longitudinal edge of the absorbent element 2. The height H may vary on the length of the intermediate element. Generally, the height H represents between 8% and 20% (according to the size of the wearer) of the length of the intermediate element which forms a sort of hammock for the absorbent element 2, the attachment means 33 constituting the high portions of said hammock.

The maximum value of the height H is located in the middle of the length of the structure, but it may be slightly shifted. Preferably it is located at the crotch.

In accordance with a particular embodiment of the invention, the intermediate element 3 exhibits a folding at each of the ends of its longitudinal edges, this folding making it possible to create a bellow in the middle of its length and to obtain said maximum height H thereto.

According to another embodiment of the invention, in the developed state, the intermediate element 3 exhibits a barrel shape whereof the straight transversal edges, may range between 4 and 15 centimeters.

Figure 4:
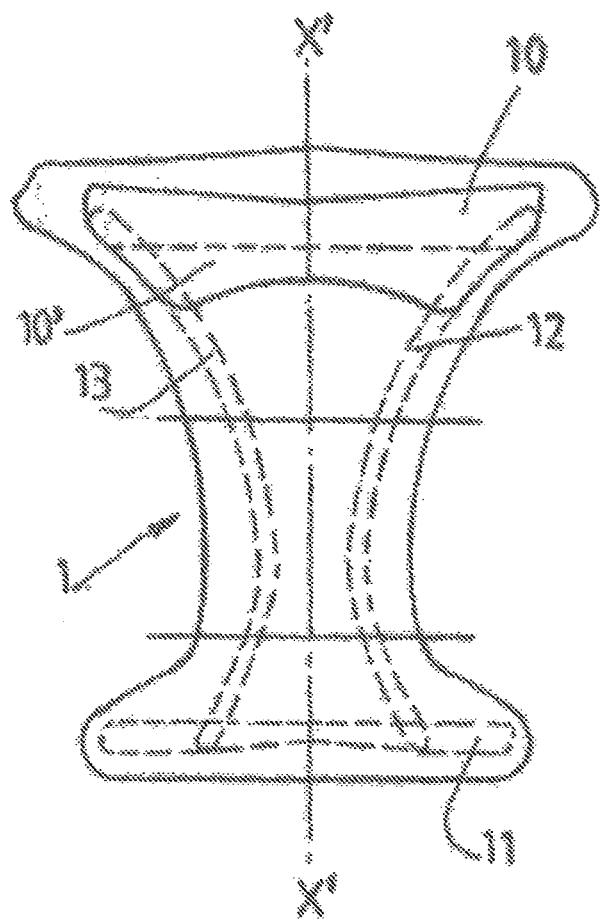
FIG. 4 a schema of the outer element, flattened.

FIG. 4 illustrates an example of an outer element 1 with a general X or hourglass shape and which is provided with a symmetrical X'X' axis which coincides with the axis XX of the structure when the latter is in place. The element 1 is reusable and preferably washable.

According to an embodiment, the outer element 1 exhibits four mechanical reinforcement areas here 10, 11, 12, 13. Two of these areas 10, 11 are substantially perpendicular to the symmetry axis X'X' whereas two other areas 12, 13 exhibit a convex curvature facing towards the symmetry axis X'X'.

According to another embodiment of the invention, the outer element 1 exhibits at least a non expansible mechanical reinforcement area 10', in direct contact with the back of the user, symmetrical with respect to axis X'X', and preferably in a butterfly shape. Any close shape, constituted of two symmetrical lobes with respect to the symmetry axis X'X' may be considered within the framework of the invention.

This characteristic ensures a good support of the structure on the body whatever the position and/or the movements of the user.

The reinforcement areas 10, 10', 11, 12, 13 may be obtained by adding a piece to the outer element 1, for example sewn, stuck, thermo-stuck, welded. One may also consider a specific knitting or even a heating technique or thermomolding of a Lycra-based (registered trademark) or other synthetic fiber-based fabric, a treatment which makes it possible to rigidify and/or to deform the heated areas, even treated by any other deformation treatment. In a known manner, this type of treatment consists in heating or thermo-heating carried out simultaneously at an extension of the concerned fabric, which allows for, once the fabric has cooled, to obtain and maintain the fabric in a permanent deformation state. If these types of treatment are carried out then the outer element will be devoid of stitching.

The width of the outer element 1, measured perpendicularly to the axis XX' is preferably lower than that of the intermediate element 3, at the crotch. This prevents wetting the outer element 1 which thus is not in contact with the pubic crease. Advantageously, a pressing of the element 1 against the intermediate element 3 is obtained according to the invention.

The outer element 1 may be constituted of an expansible material according to one or several directions such as a fabric based on natural cotton fibers, or synthetic fibers, or even, in a matter based on artificial fibers; the non expansible reinforcements may be constituted of a cotton weave or a synthetic material.

The intermediate element 3 may be a fabric coated with waterproof polyurethane. It exhibits a water repellent effect on one of its sides and is impervious on the other sides.

Figure 5:
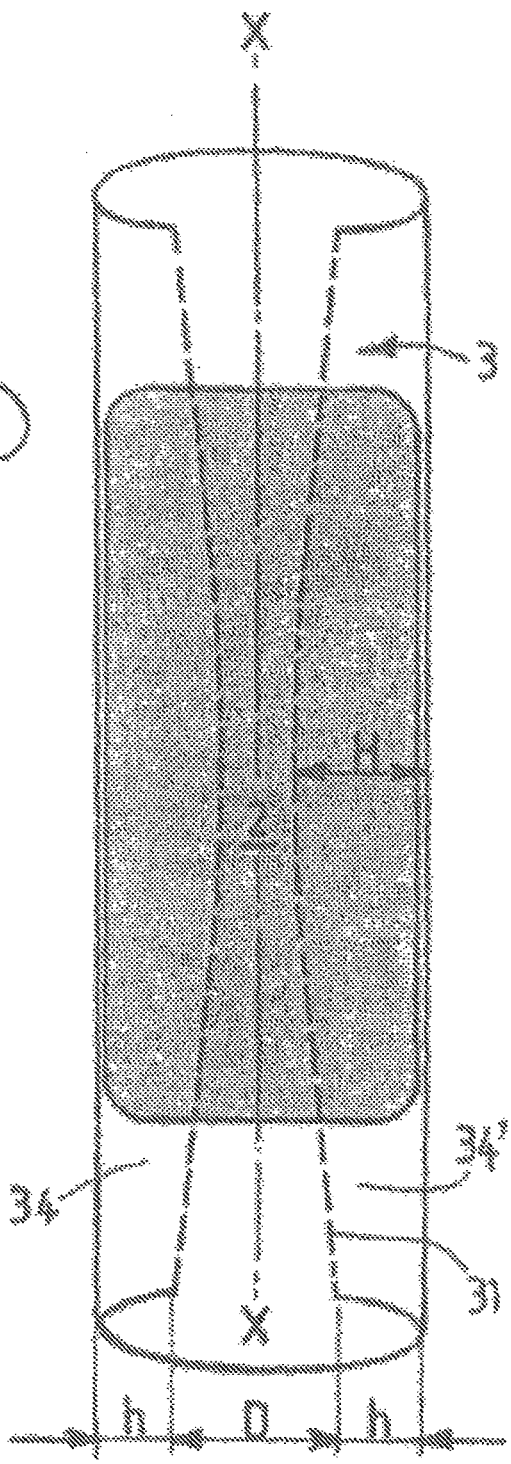
FIG. 5 a schema of the absorbent element and the intermediate element, flattened FIG. 6 a schematic transversal cross-section of a structure according to the invention, positioned on the body of a wearer.
Figure 6:
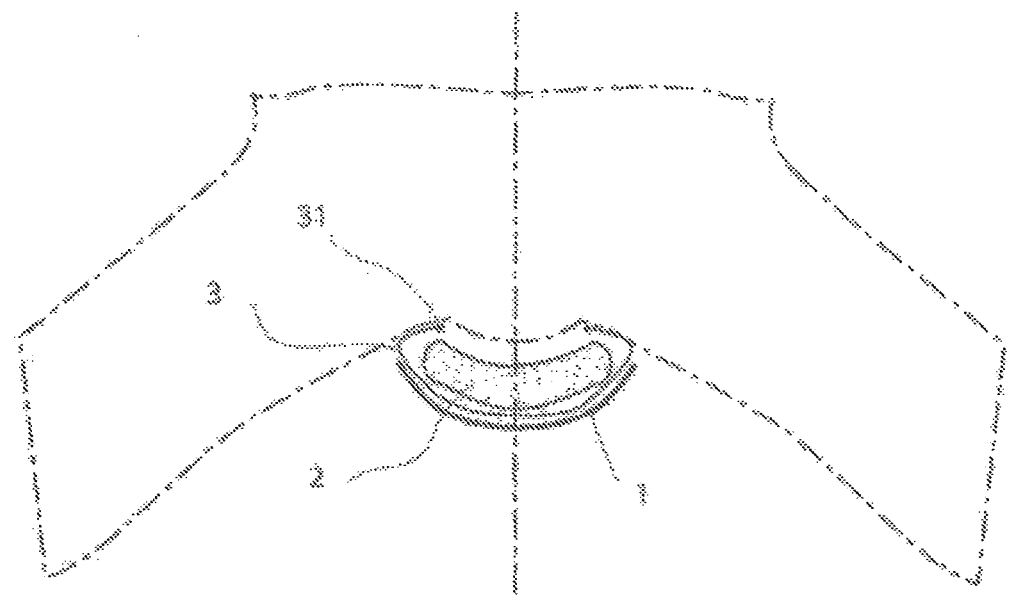

FIG. 5 shows in a very schematic manner the intermediate element 3 and the absorbent element 2 seen from the top and flattened without the fasteners 33 or the flaps 32. It becomes evident that the intermediate element 3 covers the absorbent element 2 over two longitudinal areas 34 and 34' of maximum height H. The longitudinal limits of areas 34 and 34' are respectively defined by the longitudinal edges of the absorbent element 2 and the elastic edges 31. If as is illustrated by FIG. 5 the absorbent element 2 is of rectangular shape, the elastic edges 31 will exhibit a convexity facing towards the longitudinal axis XX. If the absorbent element 2 is of hourglass shape, the elastic edges will preferably be straight.

In all cases, in usage position, a hammock of maximum depth H will form, in the middle of its length. The elastic edges 31 thus remain in permanent contact with the skin of the user, whatever his or her movements and whatever the state of the absorbent element 2. By "state" is meant the absorption level of this element 2. The state goes from a dry level, devoid of liquid, to a saturated state where the element is satiated and/or saturated with liquid and/or fecal matter.

Furthermore, as is visible on FIG. 5, each of the two transversal ends of the element 3 exhibits an equal length to: D+4×h; h being the half width covering of the element 3 on the element 2, and D+2×h being the maximum width of the absorbent element 2.

It can be seen the outer support element 1, the intermediate element or impervious hammock 3, and the absorbent element 2 closest to the pubic region. The elastic borders 31 are found to be inserted and wedged in the pubic crease thus allowing for a tightness in this area. Outside this area i.e., at the groin and outer thighs and at the lower part of the buttocks, the borders 31 remain in permanent contact with the skin of the user. This is due particularly to the specific and conjugated forms of said borders 31 and of the absorbent element 2, such as clarified above.

Thus, the intermediate element 3 is not "freely" suspended as it is permanently maintained against the wearer.

Figure 7:
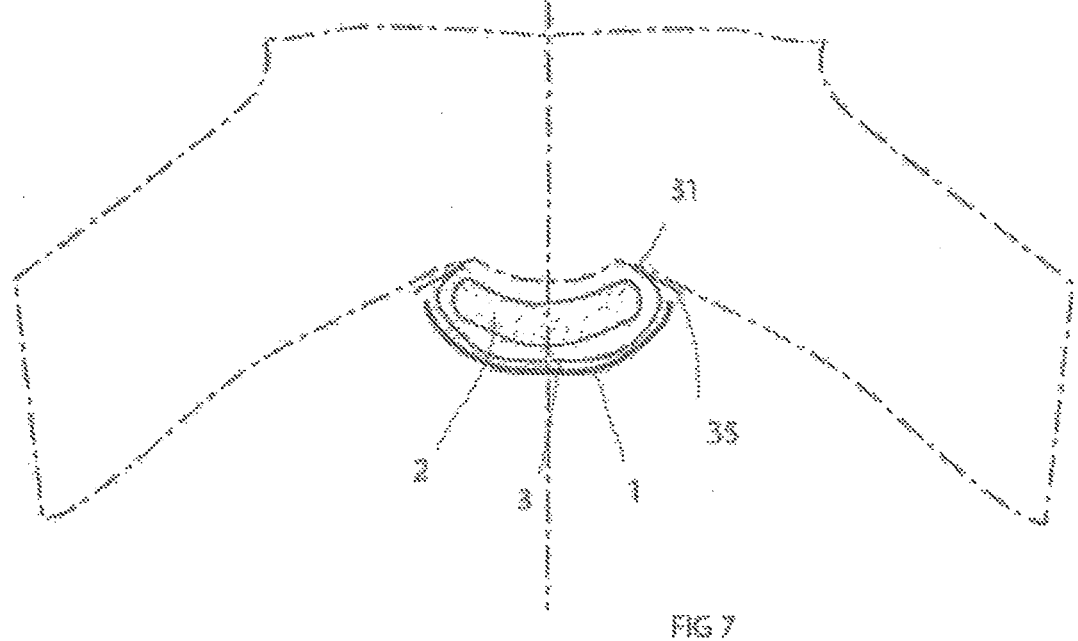
FIG. 7 a schematic transversal cross-section of a structure according to another embodiment of the invention, in position on the body of a wearer.

FIG. 7 illustrates another embodiment of the invention which differs from that which has just been described by the additional presence of longitudinal wings 35 each coming from the elastic borders 31 and which surpass outwardly. The wings 35 make it possible to move the residual humidity away with respect to the outer element 1 of the structure. They, thus reinforce the tightness. As is apparent on FIG. 7, the wings 35 are pressed against the skin thus making it possible to better distribute the humidity and thus to improve the evaporation.

Furthermore, the invention relates to a sleeve intended to cover the entire or a portion of the absorbent element 2 which may be part of a structure such as described above.

The sleeve may be or may not be weaved, degradable and/or disintegratable. It is disposable.

It is intended to retain the non fluid bodily secretions and to let pass the other secretions. Its porosity particularly will determine the type and the limit between these types of secretions.

Thus, it is possible, by detaching the sleeve from the rest of the structure to extract the non fluid secretions such as fecal matter, and to throw away this assembly down the toilet for example. The absorbent element 2 may thus be enveloped again in a new sleeve and/or washed separately. The sleeve prevents the contact of the fecal matter with the absorbent element 2 which should however be washed between every change. In the absence of a sleeve, it would be necessary to separate the fecal matter adhering to the absorbent element first (intervention not appreciated by users), before considering to introduce the absorbent element in a washing machine. This step not only induces an unpleasant or even unacceptable handling for the user, but further requires additional water consumption.

According to the invention the sleeve can be disposed of down the toilet and/or in a trash can whereas the absorbent element may be directly introduced into a washing machine, amongst any another dirty washing. The handling of such an absorbent structure is thus reduced to a minimum and should be kept as clean as possible.

The following description relates to a preferred embodiment as well as different alternatives.

Figure 10:
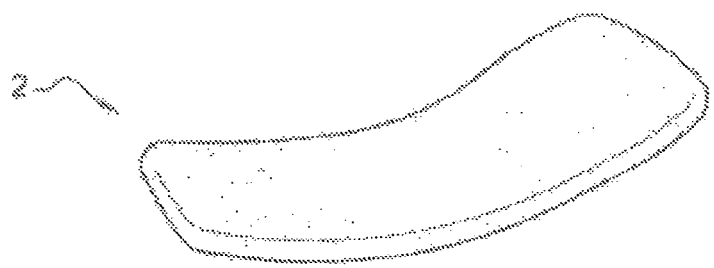
FIGS. 8 to 10 respectively illustrate a side view of an outer envelope, of an intermediate element and of an absorbent element of a structure according to another embodiment of the invention.
Figure 8:
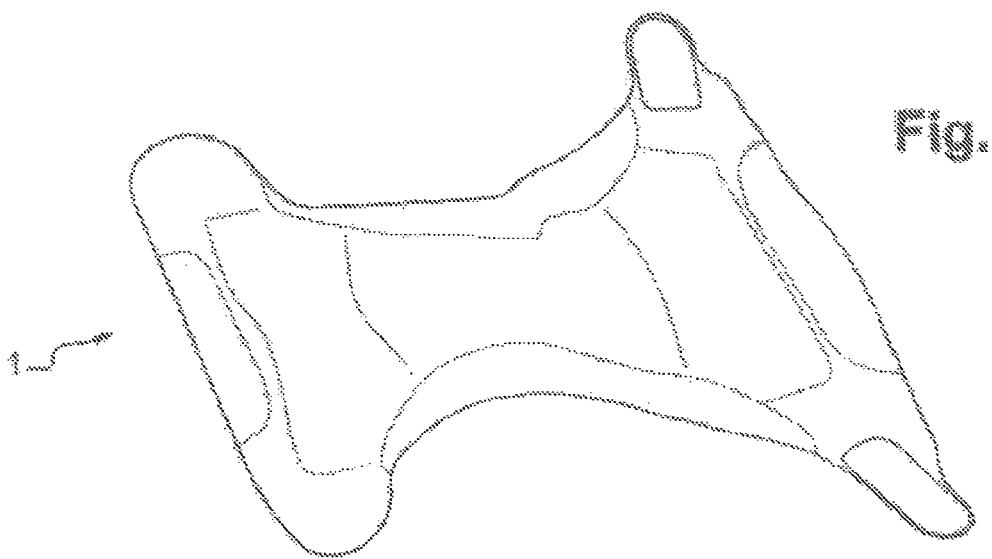

The diaper is constituted:
of an outer envelope (1), represented in FIG. 8, generally achieved in fabric, and preferably a fabric with elastic fibers, for example spandex, a derivative of polyurethane. This outer envelope (1) is reusable and washable.
of an intermediate element (3), represented in FIG. 9, generally achieved in an impervious or waterproof polyurethane-coated textile, such as Gortex®. This intermediate element is also preferably reusable and washable. The fabric of the intermediate element exhibits a full weight characteristic (fabric+coating) of around 105 g/m2 with +−30 g/m2.
of an absorbent element (2), represented in FIG. 10, either disposable to single-use, for example a lining composed mainly of cellulose or washable and reusable, or in absorbent fabric such as hemp, cotton, bamboo, and/or synthetic fiber.

The intermediate element (3) forms a sort of pocket or hammock, fastened to each transversal end on the outer element (1). This intermediate element (3) contains the absorbent element (2) and ensures tightness.

Figure 9:
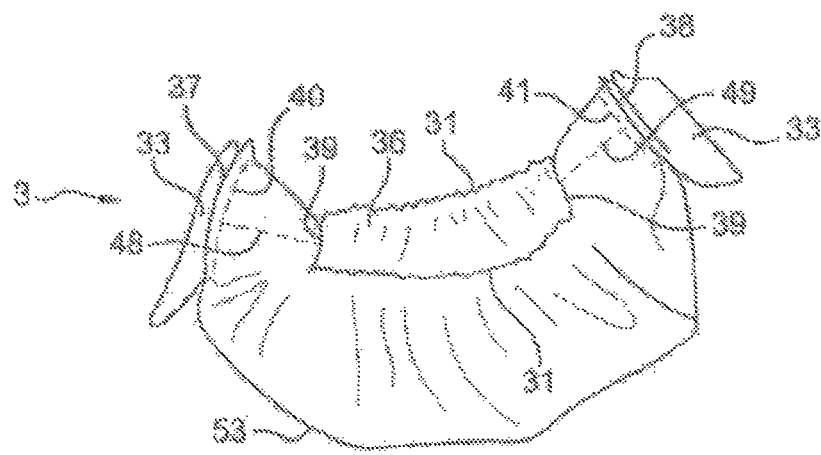

At rest, the intermediate element (3) represented in FIG. 9 exhibits a pocket (53) whereof the aperture (36) exhibits a transversal section smaller than the transversal section of the pocket in its largest width.

Particularly, the width of the aperture (36) according to a transversal axis is lower than the width of the pocket (53) at rest, measured in the plane of section where the pocket is the most swollen.

Likewise, the length of the aperture (36) according to a transversal axis is lower than the width of the pocket (53) at rest, measured in the plane of section where the pocket is the most swollen.

Is meant by "at rest" the situation wherein the pocket is maintained by its two transversal ends 37, 38 as long as there is no traction according to a longitudinal axis.

At rest, the aperture (36) exhibits, seen from the top, a rectangle shape, with longitudinal edges (31) and two substantially rectilinear transversal edges (39). The pocket (53) exhibits a barrel shape truncated according to a longitudinal cross-section. The fabric forming the pocket is puckered along the two longitudinal edges, with raw edges, without stitching, hemline or folding. The puckering is formed for example with a sewing machine comprising a straight stitching function, with an elastic thread introduced inside the bobbin to form an elastic stitch.

The puckering may be replaced by a hemline inside which is placed an elastic maintained at its two ends.

The deformation ratio (or "relative lengthening") of the elastic are higher than 100%, advantageously of 120%. In other terms, when a traction is exerted on the ends of the longitudinal edge (31), the length is doubled with respect to the dimension at rest. The lengthening is checked under constraint, once the elastic is put in place on the aperture (36). This elasticity may be obtained by stitching one, two or even three rows of elastics.

The maximum extension is obtained when a stress equivalent to a strength exerted by a weight of around 200 to 250 grams is exerted.

The transversal edges (39) do not comprise any puckers nor elastic.

The cut-out of fabric exhibits two convex portions such as represented on FIG. 5. When the pocket is shaped, this configuration is translated by the swollen shape of the pocket.

The intermediate element (3) further exhibits two welding or sealing stitches (40, 41). These stitches (40, 41) may be achieved by thermo-welding, ultrasonic welding or any other equivalent means preventing the diffusion towards the outside of the intermediate element of humidity or liquid.

The intermediate element (3) is prolonged beyond these sealing stitching (40, 41) by fasteners (37,38).

Figure 12:
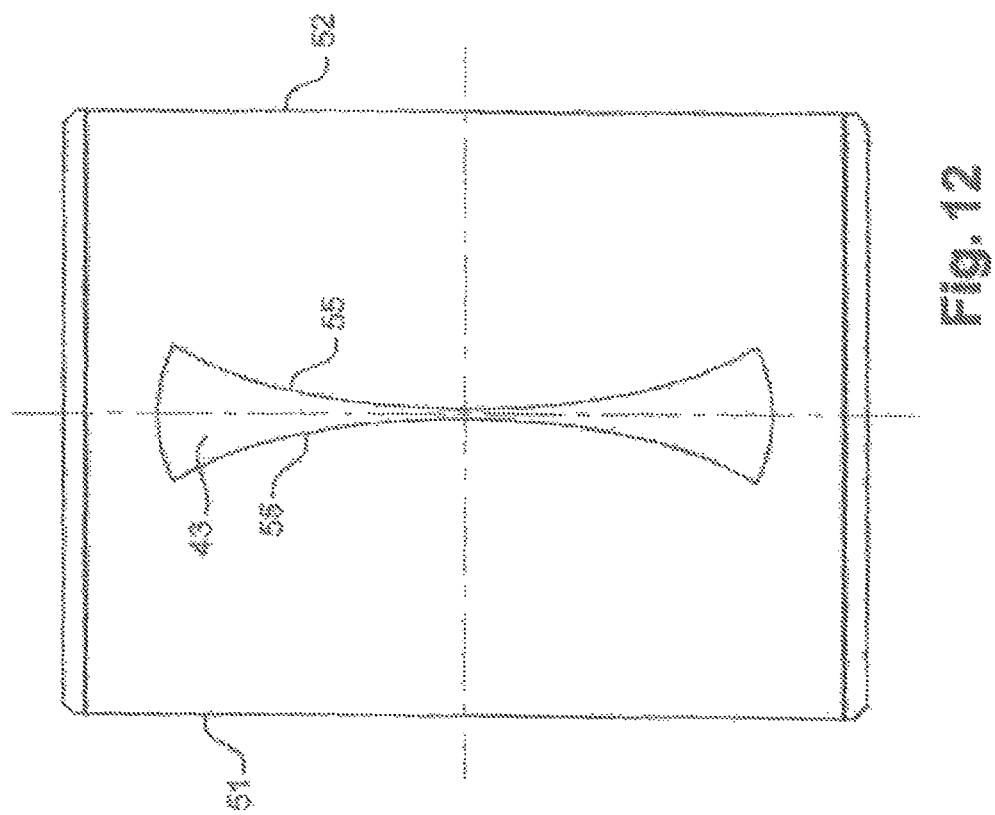
FIG. 12 represents a second embodiment of a cut-out for the realization of the intermediate element such as represented in FIG. 9.
Figure 11:
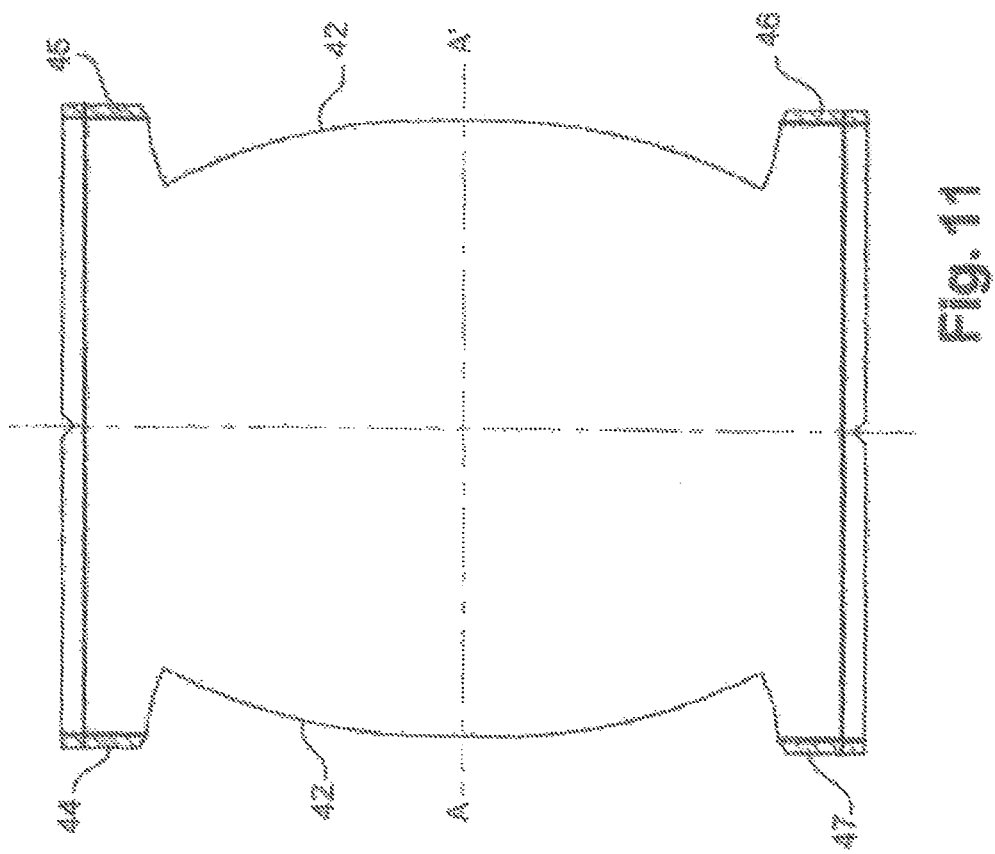
FIG. 11 represents a first embodiment of a cut-out for the realization of the intermediate element such as represented in FIG. 9.

The intermediate element (3) is achieved based on a cutout whereof FIGS. 11 and 12 represent two alternatives.

The material used for the intermediate element (3) is a synthetic fabric based on thermoplastic, for example polyurethane, making it possible to assemble by ultrasonic friction or fusion, with a polyamide or polyester mesh, coated with polyurethane.

FIG. 11 shows a first cutout alternative. The cutout is substantially rectangular. The longitudinal side exhibits a symmetrical concave edge (42) in the example described with respect to the median transversal axis (AA'), with an increasing bend radius on either side when moving away from the median axis. The length of the concave edge (42) ranges between 65% and 90% of the total length and of 78% in the described example. The minimum width of the cutout is of 79% of the maximum width of the cutout.

The intermediate element (3) is formed by folding this cut-out and sealing stitching or longitudinal sealing welding (48, 49) of the two legs respectively (44, 45) and (46, 47) longitudinal to form a pocket. This solution improves the tightness.

FIG. 12 represents an alternative embodiment, different from the previous one due to the fact that the cut-out exhibits a central recess (43) with two longitudinal edges (55) symmetrically curved with respect to a median transversal axis. The maximum width of this recess is of 11% of the width, and the maximum length of the central recess (43) ranges between 65% and 90% of the total length and of 78% in the described example.

The intermediate element (3) is formed by folding this cut-out and sealing stitching or longitudinal sealing welding of the two longitudinal edges (51, 52) longitudinal to form a pocket. This solution prevents a stitching translated as a slight extra thickness comes into contact with the skin and creates possible irritations.

This intermediate element (3) is fixed on the outer element (1) by means of attachment means (33). These fasteners are formed by a semi rigid strip, non elastically deformable, non expansible, sewn or welded to the transversal end (37, 38) of the pocket. The strip may be achieved by a superimposition of several textiles or a thermoplastic strip formed with a profile section giving it a sufficient semi-rigidity to ensure the hanging in a strap provided on the outer element, but limited so as not to cause any annoyance for the wearer of the nappy and to not make the unhanging while replacing the internal element difficult.

Figure 13:
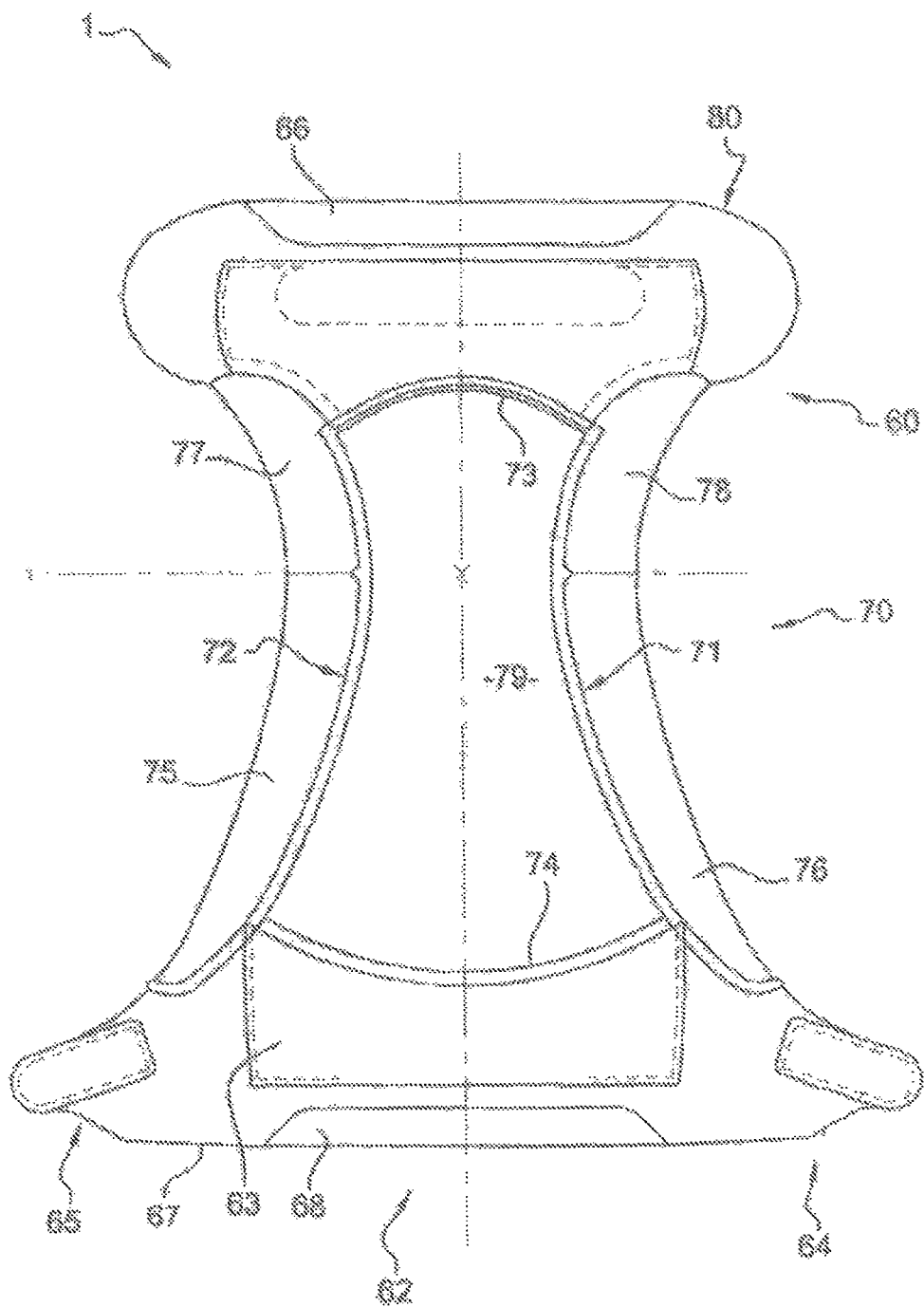
FIG. 13 represents a top view of the outer envelope such as represented in FIG. 8.

FIG. 13 represents a view of the outer element. This element is dissymmetrical with respect to the transversal plane, and exhibits a ventral portion and a dorsal portion. It is symmetrical with respect to the longitudinal axis.

The general shape is that of a bilboquet.

The ventral portion (60) is non expansible or slightly expansible, in order to prevent sagging around the abdominal belt of the wearer when he/she moves. In the example described, the transversal border (80) exhibits a supple and expansible yoke (66) to improve the comfort. This yoke exhibits a width of around two thirds of the width, and a depth of around 3 centimeters.

The dorsal portion (62) exhibits a non expansible central area (63) extended on either side by two lateral areas (64, 65) which can be slightly expansible.

In the example described, the transversal border (67) exhibits a supple and expansible yoke (68) for improved comfort. This yoke exhibits a width and a depth substantially identical to those of the yoke (66) of the ventral portion.

The crotch portion (70) is formed by an expansible piece of fabric, exhibiting two concave longitudinal edges (71, 72), and a transversal edge (73) convex on the ventral side.

The crotch portion exhibits on each side of the ventral portion a supple non puckered area (77, 78), without tightening on the thigh when the nappy is worn.

On the other hand, the supple area (75, 76) of the dorsal side is puckered on the edges (72, 71) to make the outer element (1) closer to the thigh of the wearer.

The accumulated width of the supple areas (75 to 78) measured at the median transversal axis ranges between a third and half of the width of the median area (79) at its narrowest portion.

These supple areas (75, 76) are sewn under extension on the median area (79), in order to create a puckering ensuring a flap of the intermediate element on the wearer.

On the dorsal side, the transversal edge (74) is concave for nappies of newborns, and straight or convex for the other applications, in order to promote the stretching possibilities, during the movements of the user.

A non expansible lining piece may be provided to reinforce the dorsal portion. This reinforcement may also be obtained by locked meshes in the case of manufacture by 3D knitting, a manufacturing technique called "seamless".

The ventral portion (60) and the dorsal portion (62) form, when the nappy is in place, an abdominal belt ensuring a good hold on the body of the wearer. The crotch portion is suspended with respect to this abdominal belt, and exhibits an elasticity which makes it possible to form a retention netting of the intermediate element. The depth of this crotch portion is lower than the depth at rest of the pocket (53) of the intermediate portion in order to maintain the contact between the intermediate element (3) and the body of the wearer and prevent the fabric of the outer element from coming into contact with the body of the wearer.

According to an alternative embodiment of the invention, which differs from that previously described with reference to FIG. 7, the intermediate element (3) may comprise impervious additional transversal wings, arranged longitudinally on either side of the swollen areas (34, 34'). Each one is longitudinally assembled on the swollen areas (34, 34') by a sealing welding. These wings are puckered by an elastic fixed according to the longitudinal axis of each wing. These puckered wings bring the lateral edges of the pocket (53) in contact with the skin of the wearer at the crotch, they prevent the lateral edges of the supple areas (75 to 78) of the outer envelope 1 to come into contact with the elastic borders 31 of the intermediate element 3 at the crotch. These puckered wings make it possible to keep the residual humidity away with respect to the outer element 1 of the structure.

According to another embodiment of the invention, the absorbent element (2) may be fixed by its two ends to the intermediate element (3). The advantage of such an embodiment is to not have to construct the diaper before placing it on the wearer, thus, leading to a highly appreciable important time saving, for example by the staff of a day-care center or a maternity ward.

This connection is carried out by means of 2 strips of fabric connecting each end of the absorbent element (2) to the intermediate element (3). These two rectangular-shaped connecting strips are made from impervious fabric. Their length is the width of the ends of the absorbent element (2). They are fixed to each end of the absorbent element (2) by a stitching according to one of their longitudinal edge. Their opposing longitudinal edge is welded inside the pocket (53) of the intermediate element (3) according to the sealing weldings (40, 41), or by a new sealing welding parallel to the weldings 40 and 41. Thus, these strips make it possible to advantageously connect the 2 elements (2) and (3) without there being a risk of diffusion of the humidity or liquid towards the outside of the intermediate element.

The invention claimed is:

1. A reusable absorbent diaper type structure comprising:
an outer support element, with tightening areas at apertures for the passage of thighs, configured to be adjusted to the body of a user;
a flat absorbent element;
an intermediate impervious element configured to support the absorbent element, the intermediate impervious element being connected by connectors to the outer element, the intermediate impervious element exhibiting two longitudinal elastic borders, each of which, in a stretched and flattened state, makes it possible to cover at least a longitudinal area of the absorbent element,
wherein a length of the outer support element, measured along a longitudinal median line of the outer support element, from a first of the connectors to a second of the connectors, is smaller than a length of the intermediate impervious element, measured along a longitudinal line of the intermediate impervious element, from the first of the connectors to the second of the connectors, such that the two longitudinal elastic borders are adapted to remain in permanent contact with the skin of the user, the length of the outer support element and the length of the intermediate element being measured when the outer support element is in a flattened state without the tightening areas and the intermediate impervious element is in a flattened state without the elastic borders.

2. The structure according to claim 1, wherein said borders exhibit in the stretched and flattened state, a convexity facing towards the longitudinal line.

3. The structure according to claim 1, wherein a maximum distance H measured perpendicularly to the longitudinal line, between each of the two longitudinal elastic borders and a longitudinal edge of the absorbent element is higher than 3 cm.

4. The structure according to claim 1, wherein the outer element is reusable.

5. The structure according to claim 1, wherein the absorbent element is reusable.

6. The structure according to claim 1, wherein the connectors are arranged along the width of the absorbent element and comprise reversible attachment elements.

7. The structure according to claim 1, wherein the connectors are arranged along the width of the absorbent element and comprise unremoveable attachment elements.

8. The structure according to claim 1, wherein the outer element exhibits a general X shape and comprises a symmetrical axis X'X' which coincides with the longitudinal median line.

9. The structure according to claim 1, wherein the outer element exhibits at least a mechanical reinforcement area adapted to be in dorsal contact with the user, the mechanical reinforcement area being symmetrical with respect to the longitudinal median line and butterfly-shaped.

10. The structure according to claim 1, comprising a disposable sleeve, covering at least the surface of the absorbent element, the disposable sleeve being adapted to be in contact with the skin of the user.

11. The structure according to claim 1, wherein the intermediate element further comprises longitudinal wings connected to each of its elastic longitudinal edges.

12. The structure according to claim 1, wherein a dimension of the outer element measured perpendicularly to the longitudinal median line is lower than a dimension of the intermediate element at a crotch of the user such that said outer element is adapted not to be in contact with the pubic crease of the user.

13. The structure according to claim 4, wherein the outer element is washable and elastic.

14. The structure according to claim 5, wherein the absorbent element is washable.

15. The structure according to claim 1, wherein each connector is constituted of a semi rigid strip.

16. The structure according to claim 1, wherein the first of the connectors is arranged to provide a connection between a first end, along the longitudinal line, of the intermediate impervious element, and a first end, along the longitudinal median line, of the outer support element and the second of the connectors is arranged to provide a connection between a second end, along the longitudinal line, of the intermediate impervious element, and a second end, along the longitudinal median line, of the outer support element.

17. A reusable absorbent diaper type structure comprising:
an outer support element, with tightening areas at apertures for the passage of thighs, configured to be adjusted to the body of a user;
an intermediate impervious element, and
a flat absorbent element that is removably supported by the intermediate impervious element, the flat absorbent element comprising an upper surface adapted to be in contact with the body of the user,
wherein the intermediate impervious element is connected by connectors to the outer support element, the intermediate impervious element exhibiting two longitudinal elastic borders that, in a stretched and flattened state of the intermediate impervious element, each define an edge of a longitudinal area of the intermediate impervious element that at least partly covers the upper surface of the flat absorbent element along an entire longitudinal length of said flat absorbent element, and
wherein a length of the outer support element measured along a longitudinal axis XX of said structure from a first of the connectors to a second of the connectors, when the outer support element is in a flattened state without the tightening areas, is lower than a length of the intermediate impervious element measured along the same longitudinal axis XX, from the first of the connectors to the second of the connectors, when said intermediate impervious element is in a flattened state without elastics that form the longitudinal elastic borders, such that the longitudinal elastic borders are adapted to remain in permanent contact with the skin of the user.

18. The structure according to claim 17, wherein the first of the connectors is arranged to provide a connection between a first end, along the longitudinal axis XX, of the intermediate impervious element, and a first end, along the longitudinal axis XX, of the outer support element and the second of the connectors is arranged to provide a connection between a second end, along the longitudinal axis XX, of the intermediate impervious element, and a second end, along the longitudinal axis XX, of the outer support element.

* * * * *